United States Patent [19]
Mizukami et al.

[11] Patent Number: 6,031,122
[45] Date of Patent: Feb. 29, 2000

[54] PROCESS FOR PRODUCING DIALKYL CARBONATE

[75] Inventors: Masamichi Mizukami; Yoshihisa Arai; Hidefumi Harada; Takuo Ohshida; Hiroaki Ohgi, all of Tsukuba, Japan

[73] Assignee: Mitsubishi Gas Chemical Company, Inc., Tokyo, Japan

[21] Appl. No.: 09/038,623

[22] Filed: Mar. 12, 1998

[30] Foreign Application Priority Data

Mar. 17, 1997 [JP] Japan .................................. 9-063147
Apr. 3, 1997 [JP] Japan .................................. 9-085251
Aug. 18, 1997 [JP] Japan .................................. 9-221563

[51] Int. Cl.⁷ .................................................. C07C 68/00
[52] U.S. Cl. .................................................. 558/277
[58] Field of Search ............................................. 558/277

[56] References Cited

U.S. PATENT DOCUMENTS 2,834,799  5/1958  Sowa ........................................ 558/277
4,436,668  3/1984  Harder et al. ............................ 558/277
5,534,649  7/1996  Cho et al. .

FOREIGN PATENT DOCUMENTS 10638541  2/1995  European Pat. Off. .
10709363  5/1996  European Pat. Off. .
55-102542  8/1980  Japan .
55-102543  8/1980  Japan .
57-26645  2/1982  Japan .
57-175147  10/1982  Japan .
58-079958  5/1983  Japan .
07330686  12/1995  Japan .
09255630  9/1997  Japan .

*Primary Examiner*—Michael G. Ambrose
*Attorney, Agent, or Firm*—Sughrue, Mion, Zinn, Macpeak & Seas, PLLC

[57] ABSTRACT

A process for producing a dialkyl carbonate which comprises reacting at least one member selected from the group consisting of urea and alkyl carbamate with alcohol in the presence of both a catalyst and a high boiling point organic compound having a boiling point of 180° C. or above.

17 Claims, 2 Drawing Sheets

PROCESS FOR PRODUCING DIALKYL CARBONATE

BACKGROUND OF THE INVENTION

1) Field of the Invention

The present invention relates to a process for producing a dialkyl carbonate, and more specifically, to a process for producing a dialkyl carbonate which comprises reacting at least one member selected from the group consisting of urea and alkyl carbamate with alcohol in the presence of a high boiling point organic compound. Dialkyl carbonate is a compound useful as a raw material of diphenyl carbonate.

2) Prior Art

Japanese Patent Kokai (Laid-open) No.55-102542 describes a process for producing a dialkyl carbonate by reacting urea with alcohol. Japanese Patent Kokai (Laid-open) Nos 55-102543 and 57-26645 describe a process for producing a dialkyl carbonate by reacting alkyl carbamate with alcohol. Further, Japanes Patent Kokai (Laid-open) No. 57-175147 and WO9517369 describe catalysts for above-mentioned reaction.

In known conventional processes for producing a dialkyl carbonate by reacting urea or alkyl carbamate with alcohol, a high reaction temperature of 180° C. or above and a reaction time of 8 hours or above were necessitated. The dialkyl carbonate which can be produced by the above-mentioned processes has been limited to the case used a high boiling point alcohol as the raw material. That is, when dialkyl carbonate is synthesized from both alcohol having a boiling point of 180° C. or below and alkyl carbamate, it has been necessary to conduct the reaction for a very long time or to apply a pressure in order to ensure sufficient reaction temperature since sufficiently high reaction temperature cannot be ensured due to low boiling point of alcohol.

Japanese Patent Kokai (Laid-open) No. 57-26645 discloses a process for producing a dibutyl carbonate by using both butyl carbamate and butanol as raw materials. In the process, the reaction was carried out under the condition of an applied pressure of 9 to 10 bars, but the conversion rate of carbamate after 7 hours stayed to 40%. When isobutanol was used, 40 hours were necessary to complete the reaction, so that practical reaction rate could not be obtained.

Further, when the reaction is carried out under an applied pressure, the reaction apparatus becomes complicated and requires a high cost since produced ammonia must be removed while maintaining pressure.

SUMMARY OF THE INVENTION

An object of the present invention, in order to solve above-mentioned problems, is to provide a process for producing a dialkyl carbonate in which a high reaction rate in the reaction between one member selected from the group consisting of urea and alkyl carbamate and alcohol can be ensured also in case of using low boiling point alcohol as the raw material and furthermore a dialkyl carbonate can be obtained in a simple apparatus.

As a result of extensive studies to solve above-mentioned problems, the inventors have found that it becomes possible to elevate the reaction temperature under a low pressure and above-mentioned reaction proceeds in a high reaction rate by conducting the reaction in the presence of a high boiling point organic compound. Further, surprisingly, the inventors have found also that the high boiling point organic compound provides an effect to promote the reaction and the effect to promote the reaction is larger than the effect to elevate the reaction temperature.

Moreover, the inventors have made each reactor small type by allowing the reaction to be continuous and have found that it is possible to reduce charging amount of the high boiling point organic compound and to reduce total reaction liquid amount while maintaining a high reaction temperature, i.e., a high reaction rate by applying a process which comprises reducing an initial charging amount of low boiling point alcohol to cause lowering of the reaction temperature and adding, if necessary, shortage amount of alcohol with progression of the reaction.

That is, the present invention provides a process for producing a dialkyl carbonate which comprises reacting at least one member selected from the group consisting of urea and alkyl carbamate with alcohol in the presence of both a catalyst and a high boiling point organic compound having a boiling point of 180° C. or above.

As preferable embodiment of the present invention, there is provided a process for producing a dialkyl carbonate which comprises:

feeding at least one member selected from the group consisting of urea and alkyl carbamate, a catalyst, a high boiling point organic compound having a boiling point of 180° C. or above and alcohol to a continuous multistage reactor, reacting at least one member selected from the group consisting of urea and alkyl cabamate with alcohol in the presence of both the catalyst and the high boiling point organic compound, exhausting continuously ammonia produced in each stage in a gaseous state from each stage and withdrawing continuously a reaction liquid containing dialkyl carbonate, then, feeding the reaction liquid of upper stage to a reactor of lower stage, and withdrawing the reactor liquid containing dialkyl carbonate from the lowest stage.

In the above-mentioned process of the present invention, preferably, total amount of at least one member selected from the group consisting of urea and alkyl cabamate, the catalyst and the high boiling point organic compound is introduced to first stage of the continuous multistage reactor and alcohol is additionally fed to optional stage of the continuous multistage reactor depending on reaction conditions of alcohol.

Further, the above-mentioned process comprises:

separating dialkyl carbonate from the reaction liquid obtained in the lowest stage of the continuous multistage reactor, then, returning unreacted alcohol, the catalyst, the high boiling point organic compound and carbamate as intermediate product to optional stage of the continuous multistage reactor, thereby recycling and again using both the catalyst and the high boiling point organic compound and further using as a portion of raw material both unreacted alcohol and carbamate as intermediate product.

DETAILED DESCRIPTION OF THE INVENTION

Figure 1:
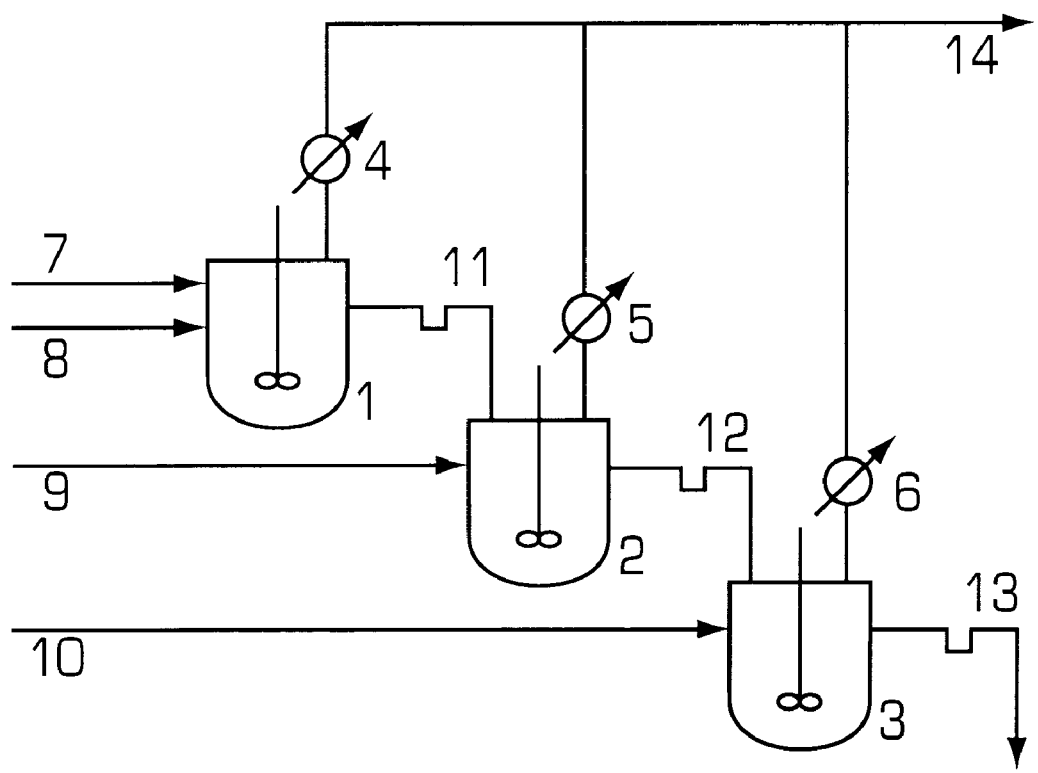
FIG. 1 is a flow sheet drawing of vessel type continuous reactor of the present invention.

The present invention will be described in detail below.

In the present invention, at least one member selected from the group consisting of urea and alkyl carbamate and alcohol are used as raw materials.

In the present invention, alkyl carbamate obtained by the reaction between urea and alcohol is an intermediate product in the process of production of the present invention. Alkyl carbamate need not be withdrawn as an intermediate product since both reaction for producing alkyl carbamate from urea and reaction for producing dialkyl carbonate from alkyl carbamate occur in series. Alkyl carbamate may be used also as raw material. Thus, in the present invention, it is possible to use again as raw material alkyl carbamate recovered in a separation step. Further, also a mixture of urea with alkyl carbamate as an intermediate product is used as the raw material.

In the present invention, alkyl carbamate is produced by the following reaction formula.

Alkyl carbamate thus produced further reacts alcohol by the following reaction formula, thereby producing dialkyl carbonate.

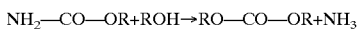

wherein R is an alkyl group and preferably an alkyl group having 1 to 10 carbon atoms.

Examples of alkyl carbamate include methyl carbamate, ethyl carbamate, propyl carbamate, butyl carbamate, pentyl carbamate, hexyl carbamate, heptyl carbamate, and octyl carbamate, in which each carbamate includes isomers thereof.

The alcohol using in the present invention is not limited on the condition it is aliphatic alcohol. Usually, alcohol having 1 to 10 carbon atoms is used.

Examples of the alcohol include methanol, ethanol, propanol, butanol, pentanol, hexanol, heptanol, octanol, nonanol and decanol, in which each alcohol includes isomers thereof.

Alcohol having carbon atoms 1 to 8 is preferable since the effect to promote a reaction rate is remarkably provided. Further, alcohol having 3 to 6 carbon atoms is more preferable.

The high boiling point organic compound (hereinafter, referred to as "high boiling point compound") using in the present invention is preferably a compound having a boiling point of 180° C. or above, more preferably a boiling point of 195° C. or above and most preferably a boiling point of 220° C. or above since the effect to elevate a boiling point is large.

The species of the high boiling point compound is not limited, but compounds to react ammonia, e.g., ketones and esters are not preferable. Although it is possible to use also amides in which it is considered to be stable for ammonia, amide with high polarity is not preferable since exhaustion of ammonia outside reaction system is prevented.

As preferable high boiling point compound, hydrocarbons and ethers are exemplified. Although hydrocarbons may be unsaturated hydrocarbons except aromatic hydrocarbons, saturated hydrocarbons and aromatic hydrocarbons with higher stability are preferable. Regarding ethers, all of aromatic ethers, aliphatic ethers and aromatic aliphatic ethers can be used.

Examples of preferable high boiling point hydrocarbons include undecane, dodecane, tridecane, tetradecane, pentadecane, hexadecane, heptadecane, octadecane, nonadecane, eicosane, tetramethyl pentadecane, dicyclohexyl, hexylbenzene, cyclohexyl benzene, heptylbenzene, octylbenzene, nonylbenzene, decylbenzene, undecylbenzene, diisopropylbenzene, triisopropylbenzene, pentamethylbenzene, methylnaphthalene, diphenylmethane, ethylbiphenyl and bibenzyl, in which each hydrocarbon includes isomers thereof.

Examples of preferable high boiling point ethers include dihexyl ether, dioctyl ether, cyclododecyl methyl ether, diethylene glycol dimethyl ether, diethylene glycol dibutyl ether, triethylene glycol dimethyl ether, tetraethylene glycol dimethyl ether, butyl phenyl ether, benzyl phenyl ether, dibenzyl ether, diphenyl ether and ditolyl ether, in which each ether includes isomers thereof.

As the catalyst of the present invention, known catalysts can be used. Japanese Patent Kokai (Laid-open) Nos.55-102542, 55-102543, 57-26645, 57-175147 describe many catalysts for the reaction which can be used in the present invention. Among them, an oxide, a hydroxide, a halide, an inorganic salt, an organic acid salt, an alkoxide, an alkyl substituted metal oxide, or an alkyl substituted metal alkoxide of a metal selected from the group consisting of zinc, magnesium, lead, copper, tin, titanium, gallium and indium are preferably used. Examples of the catalyst include zinc oxide, magnesium oxide, lead acetate, copper acetate, dibutyltin oxide, diamyltin oxide, dioctyltin oxide, dibutyldibutoxytin, diamyloxytin, tetrabutoxytitanium, tetraamyloxytitanium, gallium tributoxide, gallidium triisopropoxide, etc.

The amount of the catalyst is different depending on species of catalyst to be used and usually 0.001 to 5 mol to 1 mol of urea or alkyl carbamate.

In the present invention, dialkyl carbonate can be produced also by batch type reaction, and preferably semi-batch type reaction in which alcohol is added depending on a degree of the reaction, but it is not practical since very large reactor is required. When multistage reactor is used, dialkyl carbonate can be efficiently produced by combination of comparatively small reactors since mixing between unreacted materials and reaction liquid in which conversion has occurred, can be avoided.

It is preferable to conduct the reaction under atmospheric pressure, but it may be conducted also under a reduced pressure or under a slightly applied pressure of about 0.001 to 0.5 MPa (absolute). When the reaction is conducted under a pressure except atmospheric pressure, the reaction apparatus becomes complicated to a certain degree since a pressure-adjusting apparatus to exhaust ammonia produced during the reaction outside reaction system is required at the end of a reflux condenser.

In order to facilitate exhaustion of produced ammonia, it is preferable to conduct the reaction in the state where the reaction liquid is refluxed. That is, preferable reaction temperature is a boiling point of the reaction liquid. When the reaction progresses, alcohol is consumed, so that a boiling point of the reaction liquid is raised. The reaction may be conducted by charging initially a proper amount of alcohol and allowing the reaction temperature to be free with progress of the reaction or continued by adding properly alcohol and maintaining a boiling point of the reaction liquid to a suitable temperature. The reaction temperature is 100 to 260° C., preferably 140 to 260° C. and more preferably 160° C. to 240° C.

The reaction time is 1 to 20 hours and preferably 3 to 10 hours.

The reaction is not necessarily completed since alkyl carbamate as intermediate product is recovered to use as the raw material.

The amount of alcohol is usually 1 to 10 mol as total amount added to each reactor to 1 mol of urea and preferably 1.5 to 3 mol to 1 mol of urea. When alkyl carbamate is used or contained as the raw material, it is preferable to add further usually 0.5 to 5 mol of alcohol to 1 mol of alkyl carbamate and preferably 0.8 to 1.5 mol of alcohol to 1 mol of alkyl carbamate. Total amount of alcohol may be introduced into first reactor. However, when a large amount of alcohol is initially charged to the reactor, the boiling point of the whole reaction liquid is lowered since alcohol has the lowest temperature among the reactants, so that the reaction temperature is lowered and the reaction rate is decreased. Therefore, it is efficient to add alcohol depending on progress of the reaction to each reactor.

The amount of the high boiling point compound is usually 0.1 to 20 mol to 1 mol of urea or alkyl carbamate and preferably 1 to 10 mol to 1 mol of urea or alkyl carbamate. When alkyl carbamate is contained as the raw material, it is preferable that it is 1 to 10 times by mol to total mol of both urea and alkyl carbamate. When alcohol having a low boiling point is used, it is preferable that mol fraction of the high boiling point compound is high since the boiling point of the reaction liquid, i.e., the reaction temperature becomes high. However, when the amount of the high boiling point compound is increased, the size of reactors become large. Thus, the most suitable amount is different depending on both species and concentration of alcohol.

The reaction of the present invention is conducted at the boiling point of the reaction liquid or at a close temperature thereof. When the reaction liquid is used as it is, satisfactory reaction rate cannot be obtained since the boiling point of alcohol to be used in the present invention is lower than necessary reaction temperature. Thus, in the present invention, the high boiling point compound is used. The high boiling point compound provides both effect to elevate the reaction temperature and effect to exhaust easily ammonia from the reaction liquid by decreasing polarity of the reaction liquid.

In a continuous process, the process of the present invention can be attained by connecting vessel type reactors to conduct multistage reaction and adding properly alcohol to each reactor. That is, the liquid temperature of each reactor is set in advance, and when the liquid temperature is elevated with progress of the reaction and exceeds the setting temperature, alcohol may be added so that the liquid temperature may approach to the setting temperature. The procedure can be automatically conducted by combination of both a temperature detector and a pump. When the procedure is more simply conducted, it is attained also only by feeding a specified amount alcohol to every reactor without adjusting the temperature.

The reaction liquid is continuously withdrawn from the lowest stage reactor to conduct separation. Distillation is usually applied as the separation method. The reaction liquid contains dialkyl carbonate as the product, alcohol as the raw material, alkyl carbamate as the intermediate product, the high boiling point compound and catalyst. The remained liquid separated dialkyl carbonate is recycled to the reaction system. That is, the high boiling point compound and catalyst are again used. Alcohol and alkyl carbamate are used as the raw material.

The reactor to be used in the present invention is optional one on the condition that it is a multistage reactor. A vessel type reactor or a tower type reactor is usually used. Regarding the stage number of reactor, two stages or above and preferably three stages or above are required. When a vessel type reactor is used, it is necessary to attach a reflux condenser or a distillation column to an upper portion of the reactor and to separate alcohol from ammonia.

FIG. 1 shows an example of a continuous reaction apparatus of dialkyl carbonate using for a multistage reactor of the present invention. The production of dialkyl carbonate from both alcohol and urea is explained by FIG. 1 below.

In FIG. 1, three reactors are equipped in series. Nos. 1, 2, and 3 in FIG. 1 show each vessel type reactor, and Nos. 4, 5 and 6 show each reflux condenser. Urea, the high boiling point compound and catalyst are continuously introduced into reactor 1 via conduit pipe 7 and alcohol is introduced into reactor 1 via conduit pipe 8. After the starting of the operation, if necessary, alcohol is further added via conduit pipe 8. In each reactor, the reaction is conducted while refluxing the reaction liquid. A mixed vapor of alcohol with ammonia is generated. Alcohol is returned to each reactor by reflux condensers 4, 5 and 6 and ammonia is passed through each reflux condenser and exhausted via conduit pipe 14. The reaction liquid of reactor 1 is continuously fed to reactor 2 via conduit pipe 11. As the feeding method, an overflow method or a method for transferring the reaction liquid with a pump may be applied. When an overflow method is applied, a device to insert conduit pipe 11 below the liquid level of reactor 2 so as not to return vapor generated in reactor 2 to reactor 1 is necessary. In FIG. 1, a portion of conduit pipe 11 has been bent and sealed with the reaction liquid. Also in reactor 2, the reaction is conducted while refluxing the reaction liquid. If necessary, alcohol is further added via conduit pipe 9. The reaction liquid in reactor 2 is continuously fed to reactor 3 via conduit pipe 12. Also in reactor 3, the reaction is conducted while refluxing the reaction liquid. If necessary, alcohol is further added to reactor 3 via conduit pipe 10. The reaction liquid in reactor 3 is continuously withdrawn via conduit pipe 13 and transferred to a separation step.

As the high boiling point compound and catalyst to be introduced from conduit pipe 7, the remained liquid separated alkyl carbonate in the separation step which may contain alkyl carbamate recovered in the separation step, can be used. Further, it is not always necessary to return whole amount of the above-mentioned liquid to reactor 1. Its partial amount may be fed to reactors 2 and/or 3.

It is not always necessary to equip a stirrer in the reaction vessel. Also reactor vessel to be stirred by external circulation may be used. Also each capacity of reactors need not be uniformed. It is possible also to replace reflux condenser with distillation column. A method for treating generated vapor with one reflux condenser, e.g., a method which comprises condensing in reflux condenser 4 all vapor generated in reactors 2 and 3 and then returning to reactor 1 can be applied, but it is not preferable since alcohol concentration in each reactor comes not to be maintained. It is preferable if an apparatus which is capable of suitably distributing collected vapor to each reactor is equiiped.

In the reaction, there is a possibility that a very small amount of by-products such as ammonium cyanate, ammonium carbonate, etc., is produced to blockade pipes in a long time operation. It is preferable to maintain pipes with fear of adhesion of such by-products to more than dissociation temperature since dissociation temperature of the above-mentioned compounds is about 60° C. in atmospheric pressure. Further, it is preferable to operate reflux condenser at a temperature more than dissociation temperature of the above-mentioned compounds i.e., more than 60° C. in atmospheric pressure and below boiling point of alcohol to be used.

As the tower type reactor, conventional multistage distillation column is used as it is. The type of distillation column is not limited. A plate column type distillation column is preferable since holdup time is required. For example, plate columns used bubble cap trays, perforated plate trays, valve trays, etc., are preferable. When a tower type reactor is used, the reaction can be conducted by feeding continuously urea, alcohol, the high boiling point compound and catalyst at an upper portion or a center portion of a plate column and then withdrawing continuously ammonia in a gaseous state from an upper portion of a distillation column and simultaneously withdrawing continuously the reaction liquid from a lower portion of the distillation column. Further, in such case, it is preferable to feed continuously a mixture of urea, the high boiling point compound and catalyst at an upper portion or a center portion of the plate column and to feed alcohol from the feeding stage of the above-mentioned mixture or from plural optional stages lower than the feeding stage.

Figure 2:
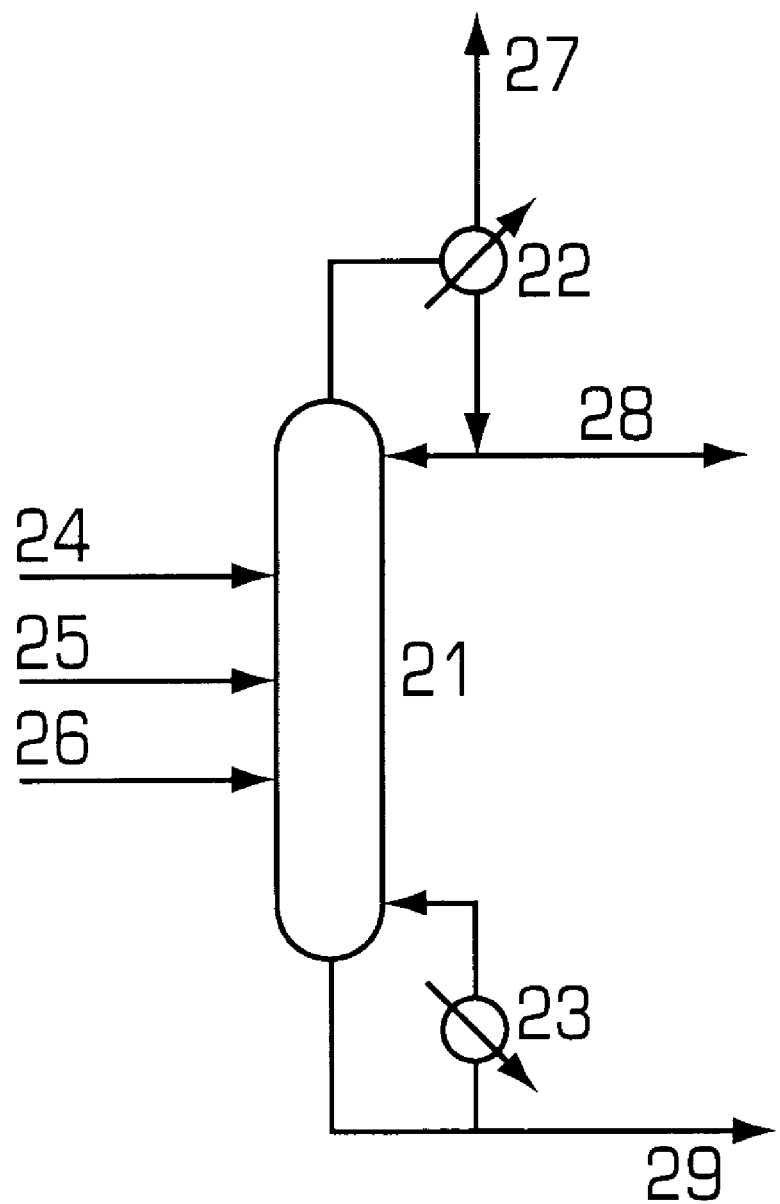
FIG. 2 is a flow sheet drawing of tower type continuous reactor of the present invention.

FIG. 2 shows one example of a continuous reaction apparatus of dialkyl carbonate used a tower type multistage reactor. The production of dialkyl carbonate from both alcohol and urea is explained by FIG. 2 below.

In FIG. 2, No. 21 shows a multistage distillation column. A mixture of urea, catalyst and the high boiling point compound is introduced from conduit pipe 24 and alcohol is introduced from conduit pipes 25 and 26. Ammonia produced in each stage of the multistage distillation column 21 reaches to column top and form a mixed vapor with alcohol to reach to reflux condenser 22, whereby alcohol is condensed in reflux condenser 22 and ammonia is passed through reflux condenser 22 and exhausted from conduit pipe 27. A portion of alcohol thus condensed is returned to column top and remained alcohol is 'fed' to conduit pipes 25 and 26 via conduit pipe 28. In each stage, the reaction liquid is fed continuously from upper stage and simultaneously a portion of the reaction liquid is withdrawn to feed continuously to lower stage. A portion of the reaction liquid reached to the lowest stage is heated through reboiler 23 to return to distillation column 21 and simultaneously remained portion of the reaction liquid is continuously withdrawn via conduit pipe 29 to transfer to a separation step.

According to the process of the present invention, ever when alcohol having a low boiling point is used, the reaction can be conducted under atmospheric pressure or a low pressure and furthermore dialkyl carbonate can be readily obtained with a high space velocity yield in a compact apparatus since the high boiling point compound promotes exhaustion of ammonia outside the reaction system and thus the reaction rate is improved. Therefore, industrial advantages of the present invention are large.

PREFERRED EMBODIMENTS OF THE INVENTION

Some of the preferred embodiments of the present invention will be described in detail below, referring to Examples, which are not intended to limit the scope of the present invention.

EXAMPLE 1

2.50 g (41.7 mmol) of urea, 7.71 g (104 mmol) of 1-butanol, 82.7 g (417 mmol) of n-tetradecane, 0.38 g (1.53 mmol) of di-n-butyltin oxide and 2.0 g of bibenzyl as internal standard substance were charged into a four-necked flask having a capacity of 200 ml, provided with a Liebig condenser, and reflux was applied while flowing warm water of 60° C. through the condenser. The reaction temperature was set to the temperature at which the liquid was refluxed.

The temperature of an oil bath used for heating was always adjusted so as to be higher by about 20° C. than the liquid temperature. The reaction liquid was sampled every one hour and change of the product was pursued by gaschromatography. The change of the reaction with elapse of time is shown below. The yield of carbonate is a value based on urea, which will be applied also to below Examples.

| Reaction time (hr) | Liquid temperature (° C.) | Yield of dibutyl carbonate (%) |
| --- | --- | --- |
| 1 | 175 | 6.4 |
| 2 | 181 | 21.6 |
| 3 | 186 | 36.5 |
| 4 | 193 | 52.4 |
| 5 | 199 | 64.9 |
| 6 | 205 | 75.5 |
| 7 | 206 | 76.7 |

EXAMPLE 2

A reflux condenser of inner diameter 34 mm and length 500 mm was attached to an autoclave of capacity 3L, made by SUS316, equipped with a stirrer, thus preparing a reactor. The reactor was equipped with a pressure adjusting valve at the end of the reflux condenser so as to be able to keep constant a pressure inside the reactor. 45.2 g (0.735 mol) of urea, 139.5 g (1.88 mol) of 1-butanol, 747 g (3.77 mol) of n-tetradecane, 6.93 g (0.028 mol) of di-n-butyltin oxide and 24.0 g of bibenzyl as internal standard substance were added to the reactor. A pressure of 0.2 MPa was applied to the inside of the reactor with nitrogen and then heating was started. The temperature was adjusted so that the reaction liquid may be refluxed. The pressure of the inside of the reactor was elevated due to generation of ammonia during the reaction, but the pressure of the inside of the reactor was maintained to about 0.2 MPa (gauge) by exhausting ammonia through the pressure adjusting value outside the reaction system. The results are shown below.

| Reaction time (hr) | Liquid temperature (° C.) | Yield of dibutyl carbonate (%) |
| --- | --- | --- |
| 1 | 191 | 0.4 |
| 2 | 207 | 17.6 |
| 3 | 218 | 37.6 |
| 4 | 223 | 51.6 |
| 5 | 227 | 67.9 |
| 6 | 230 | 72.3 |
| 7 | 230 | 73.9 |

COMPARATIVE EXAMPLE 1

94.9 g (1.58 mol) of urea, 1170 g (15.8 mol) of 1-butanol, 13.1 g (0.053 mol) of di-n-butyltin oxide and 50 g of bibenzyl as internal standard substance were added to the same reactor as in Example 2. A pressure of 0.9 MPa as applied to the inside of the reactor with nitrogen and then heating was started. The temperature was adjusted so that the reaction liquid may be refluxed. The pressure of the inside of the reactor was elevated due to generation of ammonia during the reaction, but the pressure of the inside of the reactor was maintained to about 0.9 MPa (gauge) by exhausting ammonia through the pressure adjusting value outside the reaction system. The results are shown below. When the high boiling point compound was absent, it was found that the reaction rate was decreased.

| Reaction time (hr) | Liquid temperature (° C.) | Yield of dibutyl carbonate (%) |
| --- | --- | --- |
| 1 | 188 | 0.3 |
| 2 | 201 | 5.6 |
| 4 | 199 | 17.3 |
| 6 | 200 | 29.1 |
| 8 | 200 | 39.2 |
| 10 | 200 | 49.4 |
| 12 | 200 | 57.8 |
| 14 | 199 | 63.2 |
| 16 | 200 | 67.6 |
| 18 | 200 | 71.2 |
| 20 | 200 | 72.7 |

EXAMPLE 3

The experiment was conducted in the same manner in Example 1 except that 82.7 g (308 mmol) of 2,6,10,14-tetramethyl pentadecane as the high boiling point compound was used instead of n-tetradecane and 2.0 g of o-terphenyl as internal standard substance was used instead of bibenzyl. The results are shown below.

| Reaction time (hr) | Liquid temperature (° C.) | Yield of dibutyl carbonate (%) |
| --- | --- | --- |
| 1 | 173 | 3.9 |
| 2 | 184 | 17.7 |
| 3 | 191 | 37.2 |
| 4 | 202 | 54.9 |
| 5 | 213 | 67.0 |
| 6 | 220 | 81.2 |
| 7 | 224 | 83.6 |

EXAMPLE 4

The experiment was conducted in the same manner as in Example 1 except that 76.0 g (417 mmol) of bibenzyl as the high boiling point compound was used instead of n-tetradecane and 2.0 g of o-terphenyl as internal standard substance was used instead of bibenzyl. The results are shown below.

| Reaction time (hr) | Liquid temperature (° C.) | Yield of dibutyl carbonate (%) |
| --- | --- | --- |
| 1 | 182 | 6.6 |
| 2 | 188 | 21.8 |
| 3 | 195 | 38.3 |
| 4 | 201 | 53.0 |
| 5 | 207 | 66.3 |
| 6 | 210 | 73.2 |
| 7 | 219 | 81.4 |
| 8 | 224 | 84.6 |

EXAMPLE 5

The experiment was conducted in the same manner as in Example 1 except that 71.0 g (417 mmol) of diphenyl ether as the high boiling point compound was used instead of n-tetradecane and 2.0 g of o-terphenyl as internal standard substance was used instead of bibenzyl. The results are shown below.

| Reaction time (hr) | Liquid temperature (° C.) | Yield of dibutyl carbonate (%) |
| --- | --- | --- |
| 1 | 184 | 10.5 |
| 2 | 192 | 30.0 |
| 3 | 201 | 51.3 |
| 4 | 213 | 68.2 |
| 5 | 226 | 80.6 |
| 6 | 231 | 79.8 |

EXAMPLE 6

The experiment was conducted in the same manner as in Example 1 except that 92.7 g (417 mmol) of tetraethylene glycol dimethyl ether as the high boiling point compound was used instead of n-tetradecane and 2.0 g of o-terphenyl as internal standard substance was used instead of bibenzyl. The results are shown below.

| Reaction time (hr) | Liquid temperature (° C.) | Yield of dibutyl carbonate (%) |
| --- | --- | --- |
| 1 | 198 | 2.1 |
| 2 | 203 | 8.6 |
| 3 | 209 | 19.9 |
| 4 | 213 | 30.6 |
| 5 | 217 | 39.9 |
| 6 | 219 | 49.5 |
| 7 | 220 | 53.5 |
| 8 | 220 | 55.0 |

EXAMPLE 7

2.07 g (34.5 mmol) of urea, 7.30 g (82.8 mmol) of isoamyl alcohol, 78.1 g (291 mmol) of 2,6,10,14-tetramethyl pentadecane, 0.31 g (1.25 mmol) of di-n-butyltin oxide and 2.0 g of o-terphenyl as internal standard substance were charged into a four-necked flask having a capacity of 200 ml, provided with a Liebig condenser, and reflux was applied while flowing warm water of 60° C. through the condenser. The reaction temperature was set to a temperature at which the liquid was refluxed.

The temperature of an oil bath used for heating was always adjusted so as to be higher by about 20° C. than the liquid temperature. The reaction liquid was sampled every one hour and change of the product was pursued by gaschromatography. The change of the reaction with elapse of time is shown below.

| Reaction time (hr) | Liquid temperature (° C.) | Yield of diamyl carbonate (%) |
| --- | --- | --- |
| 1 | 203 | 19.8 |
| 2 | 218 | 58.3 |
| 3 | 220 | 68.2 |
| 4 | 220 | 69.6 |

EXAMPLE 8

2.51 g (41.8 mmol) of urea, 7.71 g (104 mmol) of 1-butanol, 71.1 g (418 mmol) of diphenyl ether, 0.38 g (4.7 mmol) of zinc oxide and 2.0 g of o-terphenyl as internal standard substance were charged into a four-necked flask having a capacity of 200 ml, provided with a Liebig condenser, and reflux was applied while flowing warm water of 60° C. through the condenser. The reaction temperature was set to the temperature at which the liquid was refluxed.

The temperature of an oil bath used for heating was always adjusted so as to be higher by about 20° C. than the liquid temperature. The reaction liquid was sampled every one hour and change of the product was pursued by gaschromatography. The change of the reaction with elapse of time is shown below.

| Reaction time (hr) | Liquid temperature (° C.) | Yield of dibutyl carbonate (%) |
|---|---|---|
| 1 | 179 | 13.1 |
| 2 | 181 | 18.3 |
| 3 | 184 | 23.8 |
| 4 | 186 | 27.3 |
| 5 | 188 | 33.6 |
| 6 | 191 | 37.4 |
| 7 | 192 | 44.9 |
| 8 | 194 | 49.6 |
| 9 | 195 | 55.1 |
| 10 | 197 | 60.3 |
| 11 | 199 | 65.3 |
| 12 | 200 | 66.3 |

EXAMPLE 9

2.50 g (41.7 mmol) of urea, 13.6 g (104 mmol) of 1-octanol, 65.2 g (417 mmol) of undecane, 0.38 g (1.53 mmol) of di-n-butyltin oxide and 2.0 g of bibenzyl as internal standard substance were charged into a four-necked flask having a capacity of 200 ml, provided with a Liebig condenser, and reflux was applied while flowing warm water of 60° C. through the condenser. The reaction temperature was set to a temperature at which the liquid was refluxed.

The temperature of an oil bath used for heating was always adjusted so as to be higher by about 20° C. than the liquid temperature. The reaction liquid was sampled every one hour and change of the product was pursued by gaschromatography. The change of the reaction with elapse of time is shown below.

| Reaction time (hr) | Liquid temperature (° C.) | Yield of dioctyl carbonate (%) |
|---|---|---|
| 1 | 176 | 3.0 |
| 2 | 195 | 29.3 |
| 3 | 195 | 48.8 |
| 4 | 195 | 61.2 |
| 5 | 195 | 69.0 |
| 6 | 196 | 70.2 |

COMPARATIVE EXAMPLE 2

The experiment was conducted in the same manner as in Example 9 on the condition that 2.50 g (41.7 mmol) of urea, 67.8 g (521 mmol) of 1-octanol, 0.38 g (1.53 mmol) of di-n-butyltin oxide and 2.0 g of bibenzyl as internal standard substance were charged into the four-necked flask. That is, only 1-octanol was used instead of undecane used in Example 9. The results are shown below. Each boiling point of 1-octanol and undecane is 196° C. Although the amount of 1-octanol was increased more than Example 9, the reaction rate clearly decreased. Thus, it is clear that the advantageous effects of the high boiling point compound have been provided.

| Reaction time (hr) | Liquid temperature (° C.) | Yield of dioctyl carbonate (%) |
|---|---|---|
| 1 | 175 | 1.5 |
| 2 | 196 | 6.1 |
| 3 | 197 | 12.0 |
| 4 | 197 | 17.9 |
| 5 | 197 | 23.4 |
| 6 | 197 | 28.6 |
| 7 | 197 | 33.8 |
| 8 | 197 | 40.1 |

EXAMPLE 10

5.86 g (50 mmol) of n-butyl carbamate, 5.56 g (75 mmol) of 1-butanol, 99.0 g (369 mmol) of 2,6,10,14-tetramethylpentadecane, 0.46 g (1.9 mmol) of di-n-butyltin oxide and 2.0 g of o-terphenyl as internal standard substance were charged into a four necked flask having a capacity of 200 ml, provided with a Liebig condenser, and reflux was applied while flowing warm water of 60° C. through the condenser. The reaction temperature was set to a temperature at which the liquid was refluxed.

The temperature of an oil bath used heating was always adjusted so as to be higher by about 20° C. than the liquid temperature. The reaction liquid was sampled every one hour and change of the product was pursued by gaschromatography. The change of the reaction with elapse of time is shown below.

| Reaction time (hr) | Liquid temperature (° C.) | Yield of dibutyl carbonate (%) |
|---|---|---|
| 1 | 173 | 3.5 |
| 2 | 184 | 18.5 |
| 3 | 191 | 38.9 |
| 4 | 202 | 58.9 |
| 5 | 213 | 73.1 |
| 6 | 221 | 78.0 |

EXAMPLE 11

4.88 g (41.7 mmol) of n-butyl carbamate, 4.63 g (62.5 mmol) of 1-butanol, 82.7 g (417 mmol) of n-tetradecane, 0.38 g (1.5 mmol) of di-n-butyltin oxide and 2.0 g of bibenzyl as internal standard substance were charged into a four necked flask having a capacity of 200 ml, provided with a Liebig condenser, and reflux was applied while flowing warm water of 60° C. through the condenser. The reaction temperature was set to a temperature at which the liquid was refluxed.

The temperature of an oil bath used heating was always adjusted so as to be higher by about 20° C. than the liquid temperature. The reaction liquid was sampled every one hour and change of the product was pursued by gaschromatography. The change of the reaction with elapse of time is shown below.

| Reaction time (hr) | Liquid temperature (° C.) | Yield of dibutyl carbonate (%) |
|---|---|---|
| 1 | 176 | 15.4 |
| 2 | 181 | 29.7 |
| 3 | 186 | 44.5 |
| 4 | 191 | 62.0 |
| 5 | 198 | 74.8 |
| 6 | 203 | 78.0 |

EXAMPLE 12

7.46 g (63.7 mmol) of n-butyl carbamate, 7.08 g (95.5 mmol) of 1-butanol, 108.4 g (637 mmol) of diphenyl ether, 0.59 g (2.4 mmol) of di-n-butyltin oxide and 2.0 g of o-terphenyl as internal standard substance were charged into a four necked flask having a capacity of 200 ml, provided with a Liebig condenser, and reflux was applied while flowing warm water of 60° C. through the condenser. The reaction temperature was set to a temperature at which the liquid was refluxed.

The temperature of an oil bath used heating was always adjusted so as to be higher by about 20° C. than the liquid temperature. The reaction liquid was sampled every one hour and change of the product was pursued by gaschromatography. The change of the reaction with elapse of time is shown below.

| Reaction time (hr) | Liquid temperature (° C.) | Yield of dibutyl carbonate (%) |
|---|---|---|
| 1 | 180 | 9.5 |
| 2 | 183 | 24.7 |
| 3 | 187 | 41.1 |
| 4 | 193 | 57.0 |
| 5 | 199 | 73.5 |
| 6 | 205 | 78.0 |

EXAMPLE 13

5.0 g (38.1 mmol) of isoamyl carbamate, 5.04 g (57.2 mmol) of isoamyl alcohol, 86.0 g (320 mmol) of 2,6,10,14-tetramethylpentadecane, 0.35 g (1.4 mmol) of di-n-butyltin oxide and 2.0 g of o-terphenyl as internal standard substance were charged into a four necked flask having a capacity of 200 ml, provided with a Liebig condenser, and reflux was applied while flowing warm water of 60° C. through the condenser. The reaction temperature was set to a temperature at which the liquid was refluxed.

The temperature of an oil bath used heating was always adjusted so as to be higher by about 20° C. than the liquid temperature. The reaction liquid was sampled every one hour and change of the product was pursued by gaschromatography. The change of the reaction with elapse of time is shown below.

| Reaction time (hr) | Liquid temperature (° C.) | Yield of diamyl carbonate (%) |
|---|---|---|
| | 207 | 22.7 |
| 2 | 218 | 59.1 |
| 3 | 220 | 67.6 |
| 4 | 222 | 70.2 |

EXAMPLE 14

7.22 g (41.7 mmol) of n-octyl carbamate, 8.15 g (62.6 mmol) of 1-octanol, 65.2 g (417 mmol) of undecane, 0.38 g (1.53 mmol) of di-n-butyltin oxide and 2.0 g of bibenzyl as internal standard substance were charged into a four necked flask having a capacity of 200 ml, provided with a Liebig condenser, and reflux was applied while flowing warm water of 60° C. through the condenser. The reaction temperature was set to a temperature at which the liquid was refluxed.

The temperature of an oil bath used heating was always adjusted so as to be higher by about 20° C. than the liquid temperature. The reaction liquid was sampled every one hour and change of the product was pursued by gaschromatography. The change of the reaction with elapse of time is shown below.

| Reaction time (hr) | Liquid temperature (° C.) | Yield of dioctyl carbonate (%) |
|---|---|---|
| | 176 | 9.0 |
| 2 | 195 | 33.7 |
| 3 | 195 | 53.7 |
| 4 | 195 | 64.3 |
| 5 | 195 | 72.5 |
| 6 | 196 | 73.7 |

COMPARATIVE EXAMPLE 3

The experiment was conducted in the same manner as in Example 14 on the condition that 7.22 g (41.7 mmol) of n-octyl carbamate, 62.5 g (480 mmol) of 1-octanol, 0.38 g (1.53 mmol) of di-n-butyltin oxide and 2.0 g of bibenzyl as internal standard substance were charged into to the four-necked flask. That is, only 1-octanol was used instead of undecane used in Example 14. The results are shown below. Each boiling point of 1-octanol and undecane is 196° C. . Although the amount of 1-octanol was increased more than Example 14, the reaction rate clearly decreased. Thus, it is clear that the advantageous effects of the high boiling point compound have been provided.

| Reaction time (hr) | Liquid temperature (° C.) | Yield of dioctyl carbonate (%) |
|---|---|---|
| | 175 | 3.6 |
| 2 | 196 | 8.3 |
| 3 | 196 | 14.0 |
| 4 | 196 | 20.0 |
| 5 | 196 | 25.4 |
| 6 | 196 | 30.7 |
| 7 | 196 | 35.8 |
| 8 | 196 | 42.2 |

EXAMPLE 15

The experiment was conducted using three stages continuous reaction apparatus identical to that of FIG. 1. As reactors 1, 2 and 3, the same stirring vessels to each other having capacity of 1 L, equipped with buffle plate and a stirrer, were used. n-butanol as alcohol, diphenyl ether as the high boiling point compound and dibutyltin oxide as catalyst were used. The liquid in which urea, the catalyst and the high boiling point compound have been homogeneously dispersed in a preliminary mixing vessel was continuously introduced into reactor 1 via conduit pipe 7. Alcohol was automatically introduced via conduit pipes 8, 9 and 10 so as to maintain reaction temperature of each reactor to a specified temperature. The temperature of each reactor was set to 190° C. in reactor 1, 200° C. in reactor 2 and 210° C. in reactor 3. Heating was conducted with each oil bath attached to each reactor. Warm water of 80° C. was flowed through reflux condensers 4, 5 and 6. Overflow pipes 11, 12 and 13 were equipped so as to keep the amount of liquid constant. A portion of the overflow pipe was bent to make a liquid sealing place so that vapor generated from the reaction liquid may not go to neighboring reactor. Ammonia generated from each reactor was separated from n-butanol through reflux condensers 4, 5 and 6 and then exhausted via conduit pipe 14.

As a result of continuous reaction for 100 hours, 32.6 kg of the reaction liquid was obtained via conduit pipe 13. The reaction liquid was distilled, whereby 3850 g of dibutyl carbonate was obtained.

Total feeding amount to each reactor and yield based on urea in each reactor are shown below.

| | Total feeding amount (100 hours) | | |
|---|---|---|---|
| | reactor 1 | reactor 2 | reactor 3 |
| Urea | 2336 g | | |
| N-butanol | 4716 g | 402 g | 322 g |
| Diphenyl ether | 26342 g | | |
| Dibutyltin oxide | 359 g | | |
| Yield based on urea in each reactor | | | |
| Butyl carbamate | 61.8% | 34.7% | 18.0% |
| Dibutyl carbonate | 15.7% | 44.2% | 63.8% |

EXAMPLE 16

When dibutyl carbonate was separated by distillation in Example 15, obtained pre-distillate was mixed with distillation residue to prepare recovered liquid. It was found by analysis that the recovered liquid was composed of the following components.

| Components per 1 kg of recovered liquid | |
|---|---|
| n-butanol | 30.3 g (0.409 mol) |
| Butyl carbamate | 27.4 g (0.234 mol) |
| Dibutyl carbonate | 16.7 g (0.096 mol) |
| Diphenyl ether | 912.8 g (5.363 mol) |
| Dibutyltin oxide | 12.6 g (0.051 mol) |

The same reactors as in Example 15 were used. 290.1 g/hr of the recovered liquid thus obtained and 23.36 g/hr of urea were introduced into reactor 1 via conduit piper 7. N-butanol was automatically introduced via conduit pipes 8, 9 and 10 so as to maintain the same setting temperature as in Example 15. As a result of continuous reaction for 100 hours in the same manner as in Example 15, 34.9 kg of the reaction liquid was obtained via conduit pipe 13. The reaction liquid was distilled, whereby 5070 g of dibutyl carbonate was obtained.

Total feeding amount to each reactor and yield based on urea in each reactor are shown below.

| | Total feeding amount (100 hours) | | |
|---|---|---|---|
| | reactor 1 | reactor 2 | reactor 3 |
| Urea | 2336 g | | |
| n-butanol | 5150 g | 470 g | 354 g |
| Butyl carbamate | 796 g | | |
| Dibutyl carbonate | 486 g | | |
| Diphenyl ether | 26482 g | | |
| Dibutyltin oxide | 366 g | | |
| Yield based on urea in each reactor | | | |
| Dibutyl carbonate | 30.7% | 63.8% | 86.0% |

EXAMPLE 17

The experiment was conducted in the same manner as in Example 15 except that isoamyl alcohol as alcohol was used instead of n-butanol and the temperature of each reactor was set to 180° C. in reactor 1 and 200° C. in reactors 2 and 3.

As a result of continuous reaction for 100 hours, 27.6 kg of the reaction liquid was obtained. The reaction liquid was distilled, whereby 6588 g of diisoamyl carbonate was obtained.

Total feeding amount of each reactor and yield based on urea in each reactor are shown below.

| | Total feeding amount (100 hours) | | |
|---|---|---|---|
| | reactor 1 | reactor 2 | reactor 3 |
| Urea | 3000 g | | |
| Isoamyl alcohol | 8157 g | 419 g | 1123 g |
| Diphenyl ether | 17000 g | | |
| Dibutyltin oxide | 460 g | | |
| Yield based on urea in each reactor | | | |
| Isoamyl carbamate | 58.5% | 26.7% | 13.1% |
| Diisoamyl carbonate | 18.2% | 53.9% | 60.5% |

What is claimed is:

1. A process for producing a dialkyl carbonate which comprises reacting at least one member selected from the group consisting of urea and alkyl carbamate with alcohol in the presence of both a catalyst and a high boiling point organic compound having a boiling point of 180° C. or above.

2. The process for producing a dialkyl carbonate according to claim 1, wherein said high boiling point organic compound is a hydrocarbon or an ether, each having a boiling point of 180° C. or above.

3. The process for producing a dialkyl carbonate according to claim 1, wherein said alcohol is an aliphatic alcohol having 3 to 6 carbon atoms.

4. The process for producing a dialkyl carbonate according to claim 2, wherein said high boiling point organic compound is at least one member selected from the group consisting of tetradecane, undecane, tetramethylpentadecane, bibenzyl, diphenyl ether and tetraethylene glycol dimethyl ether.

5. The process for producing a dialkyl carbonate according to claim 2, wherein said high boiling point organic compound is at least one member selected from the group consisting of tetramethylpentadecane, tetradecane and diphenyl ether.

6. The process for producing a dialkyl carbonate according to claim 1, wherein the reaction is carried out under a pressure of 0.001 MPa (absolute) to atmospheric pressure.

7. A process for producing a dialkyl carbonate which comprises:

feeding at least one member selected from the group consisting of urea and alkyl carbamate, a catalyst, a high boiling point organic compound having a boiling point of 180° C. or above and alcohol to a continuous multistage reactor, reacting at least one member selected from the group consisting of urea and alkyl carbamate with alcohol in the presence of both the catalyst and the high boiling point organic compound, exhausting continuously ammonia produced in each stage in a gaseous state from each stage and withdrawing continuously a reaction liquid containing dialkyl carbonate, then, feeding the reaction liquid of upper stage to a reactor of lower stage, and withdrawing the reactor liquid containing dialkyl carbonate from the lowest stage.

8. The process for producing a dialkyl carbonate according to claim 7, wherein the total amount of urea or alkyl carbamate, the catalyst and the high boiling point organic compound is introduced to the first stage of the continuous multistage reactor and alcohol is additionally fed to another stage of the continuous multistage reactor.

9. The process for producing a dialkyl carbonate according to claim 7, which comprises:

separating dialkyl carbonate from the reaction liquid obtained in the lowest stage of the continuous multistage reactor, then, returning unreacted alcohol, the catalyst, the high boiling point organic compound and carbamate as intermediate product to another stage of the continuous multistage reactor, thereby recycling and again using both the catalyst and the high boiling point organic compound and further using as a portion of raw material both unreacted alcohol and carbamate as intermediate product.

10. The process for producing a dialkyl carbonate according to claim 8, which comprises:

separating dialkyl carbonate from the reaction liquid obtained in the lowest stage of the continuous multistage reactor, then, returning unreacted alcohol, the catalyst, the high boiling point organic compound, and carbamate as intermediate product to another stage of the continuous multistage reactor, thereby recycling and again using both the catalyst and the high boiling point organic compound and further using as a portion of raw material both unreacted alcohol and carbamate as intermediate product.

11. The process for producing a dialkyl carbonate according to claim 7, wherein said continuous multistage reactor has three or more reactors.

12. The process for producing a dialkyl carbonate according to claim 7, wherein a feeding amount of said high boiling point organic compound is 0.1 to 10 times by mole to that of urea.

13. The process for producing a dialkyl carbonate according to claim 7, wherein the feeding amount of alcohol in the first stage of said continuous multistage reactor is 2 times by mole or less to that of urea.

14. The process for producing a dialkyl carbonate according to claim 7, wherein said high boiling point organic compound is hydrocarbon or an ether, each having a boiling point of 180° C. or above.

15. The process for producing a dialkyl carbonate according to claim 14, wherein said high boiling point organic compound is diphenyl ether.

16. The process for producing a dialkyl carbonate according to claim 7, wherein said alcohol is an aliphatic alcohol having 3 to 6 carbons atoms.

17. The process for producing a dialkyl carbonate according to claim 7, wherein the reaction is carried out under a pressure of 0.001 MPa (absolute) to atmospheric pressure.

* * * * *